United States Patent [19]

Parnaby et al.

[11] Patent Number: 4,624,132
[45] Date of Patent: Nov. 25, 1986

[54] RHEOMETER

[76] Inventors: John Parnaby, 65 Silhill Hall Road, Solihull, West Midlands; Christopher A. M. Humphries, 57 Tormead Road, Guildford, Surrey, both of England

[21] Appl. No.: 722,165

[22] Filed: Apr. 11, 1985

[30] Foreign Application Priority Data

Apr. 12, 1984 [GB] United Kingdom ............... 8409502

[51] Int. Cl.[4] ........................................... G01N 11/08
[52] U.S. Cl. ......................................................... 73/55
[58] Field of Search ......................................... 73/55, 56

[56] References Cited

U.S. PATENT DOCUMENTS

| | | | |
|---|---|---|---|
| 1,586,948 | 6/1926 | Connet | 73/55 X |
| 1,795,250 | 3/1931 | Connet | 73/55 X |
| 1,863,090 | 6/1932 | Albersheim et al. | 73/55 |
| 1,958,878 | 5/1934 | Albersheim et al. | 73/55 |
| 1,963,011 | 6/1934 | Albersheim et al. | 73/55 |
| 2,023,568 | 12/1935 | Albersheim et al. | 73/55 X |

Primary Examiner—Stewart J. Levy
Assistant Examiner—Joseph W. Roskos
Attorney, Agent, or Firm—D. Peter Hochberg

[57] ABSTRACT

A method of determination of extensional viscosity and elasticity of a molten polymer or other fluid comprises making pressure measurements on flows of the fluid through an apparatus which includes a fluid delivery system communicating with an open ended die, the cavity of the die being shaped so as to include a converging portion and a diverging portion. The diverging and converging portions preferably intercommunicate with each other through a die cavity portion of uniform cross section. In a preferred form of the method there is also determined the shear viscosity of the fluid. The converging and diverging portions of the die are preferably symmetrically shaped with respect to each other.

7 Claims, 3 Drawing Figures

SECTION F-G.

RHEOMETER

This invention relates to a method and an apparatus for determining rheological properties of fluids, especially of viscoelastic fluids and most especially of polymer melts.

Artefacts consisting in whole or part of polymeric materials are commonly manufactured by methods that include forcing the polymeric material to flow while in a molten state. The flow forms the material into a predetermined shape, which is retained, at least approximately, after cooling and consequent solidification. Extrusion and injection moulding are examples of such shaping processes.

The design of machinery for the performance of polymer melt flow processing operations, the control of such operations and the selection of materials for the said operations are greatly assisted by a quantitative understanding of the rheological properties of the molten polymeric materials to be processed. Thus the determination of rheological properties of polymer melts is of great industrial importance. In addition, the determination of rheological properties of fluids in general is of great scientific and technological interest.

By 'molten state' is meant a state in which material behaves predominantly in a viscous fashion rather than predominantly in an elastic fashion, in response to applied forces. Usually, a polymeric material is rendered in a molten state by being heated to a temperature above a critical temperature, which may be a crystalline melting temperature or a softening temperature. However, it will be appreciated that polymeric materials behave in deformation in a partly viscous and partly elastic fashion, at all temperatures to which they are ordinarily subjected. The apparatus of the present invention is designed for the determination of rheological properties of any fluid. It is especially intended for use with viscoelastic fluids, and is most especially intended for use with polymer melts.

Throughout the present specification, the meanings of all such expressions as 'viscoelastic', 'constitutive equation', 'stress relaxation' and 'rheometer' are those that are understood generally by rheologists and are defined in standard textbooks on rheology, for example C. D. Han, 'Rheology in Polymer Processing', Academic Press, 1976 and C. J. S. Petrie, 'Elongational Flows', Pitman, 1979. In particular, by 'fluid' is meant a material whose deformation in response to an applied force is predominantly (but not necessarily wholly) viscous. Thus the term includes viscoelastic fluids and polymer melts.

The various different aspects of a fluid's rheological behavior can only be quantitatively inter-related by the use of an accurate constitutive equation. By an 'accurate constitutive equation' is meant a constitutive equation whose modelling of the deformation of the fluid to which it is applied is in close agreement with experimentally measured data. An inaccurate constitutive equation leads to inter-relationships between the said aspects of rheological behavior, that are not in accurate agreement with experimental data.

Where accurate constitutive equations are not available, as is usually the case with polymer melts, it is advantageous to the rheologist to determine a given rheological property in an experiment in which a flow is established that simulates as closely as possible the flow to the modelling of which the determined rheological property is intended to be applied. It is further advantageous that the experimental variable, from data of which the rheological property is determined, should be physically as similar as possible to the variable that it is intended to calculate from the determined rheological property. The concept defined in this paragraph is referred to as 'simulation' in the remainder of the present specification.

The invention provides a method of determination of extensional viscosity and elasticity of a fluid, by making pressure measurements on flows of the fluid through an apparatus which includes a fluid delivery system connected to one end of an open ended die, the die cavity being so shaped, as to include a converging portion and a diverging portion.

Extensional viscosity is determined generally in the art by a variety of methods, including methods based on filament stretching, on sheet stretching, on bubble inflation, on bubble collapse, on the ductless siphon, on fibre spinning and on converging flow. In converging flow experiments, a pressure drop associated with a converging flow is measured. Such experiments have been described in scientific papers by F. N. Cogswell (Polymer Engineering and Science, Vol. 2, p. 64, 1972), by R. N. Shroff, L. V. Cancio and M. Shida (Transactions of the Society of Rheology, Vol. 21, p. 429, 1977) and by D. C. Huang and R. N. Shroff (Journal of Rheology, Vol. 25, p. 605, 1981).

One disadvantage of the determination of extensional viscosity in converging flow experiments is that, in most cases of the said experiments, the fluid extension rate is not constant in the direction of convergence, and so viscoelastic transients may cause unwanted contributions to the measured pressure drop.

A second disadvantage is that the converging flow in most converging flow experiments consists of a superposition of shear flow and extensional flow. Fluid mechanical assumptions must be made in order to make it possible to substract out that part of the pressure drop caused by the shear flow component of the flow. It is also necessary to subtract out any contribution to the total measured pressure drop from shear flow in portions of the die cavity upstream from and downstream from the converging portion. Only after the shear flow contributions to the total measured pressure drop have been subtracted out can extensional viscosity be evaluated. (Shear flow can be eliminated or reduced by lubrication of the die walls).

A third disadvantage is that the transitional flows at the entrance to and at the exit from the converging portion of the die cavity introduce unpredictable (and hence uncompensatable) contributions to the measured pressure drop.

A fourth disadvantage is that storage of elastic energy occurs during the converging flow, causing a further addition to the measured pressure drop and a consequent further inaccuracy in the evaluation of the extensional viscosity.

A fifth disadvantage is that a certain amount of mathematical simplification and averaging must be applied in the treatment of experimental pressure drop data relating to the converging flow system, in order to make it possible to evaluate extensional viscosity from the data.

Converging flow experiments have the advantage over other types of experiment for the determination of extensional viscosity, that higher extension rates may be obtained. Converging flow experiments may be considered further advantageous if the converging nature of the flow upon which the determination is based gives rise to the property of simulation, as herein defined, in relation to the type of flow problem that it may be desired to treat. Elements of converging flow are very common in polymer melt processing machinery, and the extension rates encountered are often relatively high, and so the two said advantages are of considerable practical importance.

The determination of rheological properties relating to the elastic aspects of the rheological behavior of fluids, and especially of polymer melts, is beset by problems arising from the limitations of constitutive models, to a much greater extent than is the determination of rheological properties relating to the viscous aspects. Consequently, in the determination of fluid elastic properties, it is even more preferable than in the determination of viscous properties, that the flow upon which the property determination is based should possess the property of simulation, as herein defined, in relation to the flow to which the determined property is intended to be applied.

Various rheological properties relating to the elastic aspects of the rheological behavior of fluids are commonly used. Examples are shear compliance, elongational compliance, shear modulus, elongational modulus, stress relaxation time, recoverable strain and the first and second normal stress functions. Inter-relationships between groups of these properties exist, but these inter-relationships are dependent upon the choice of constitutive model. Similarly, relationships between the properties and experimental data are dependent upon the choice of constitutive model. In the Example of the present specification, the shear modulus is selected as the elastic property to be determined from experimental data taken from the novel rheometer, and certain constitutive assumptions underlie the equations used to obtain the shear modulus from measured data. However, this should not be taken to imply any limitation as to the generality of the method of measuring elastic rheological properties according to the present invention; it will be appreciated that the method and apparatus of the present invention could be applied using different constitutive assumptions, and in such a way as to lead to determinations of different fluid elastic properties. By the term 'fluid elasticity' as used in the present specification is meant any rheological property relating to the elastic aspects of rheological behavior, having regard to the foregoing comments.

Elastic rheological properties have been calculated from experiments on post extrusion swelling, on normal stress differences, on stress relaxation, on strain recovery, on dynamic shearing, on startup flow, on rod climbing and on entrance pressure drops. In entrance pressure drop experiments, the pressure drop associated with flow from a reservoir into a circular capillary die or into a rectangular slit die is measured. (This pressure drop is subtracted from the total pressure drop by the Bagley end correction procedure in experiments to determine shear viscosity.) The entrance pressure drop can be used to determine fluid elasticity because a substantial component of the entrance pressure drop derives from the reversible storage of elastic energy in the flow from reservoir to die. Determination of fluid elasticity from measurements of entrance pressure drop often has the advantage over other methods, of simulation as herein defined. A disadvantage of elasticity determination by the entrance pressure drop method is the difficulty of estimating, and hence of compensating for, viscous and irreversible elastic contributions to the measured entrance pressure drop.

A converging flow is here defined as a flow in which the streamlines converge in the direction of flow, in consequence of a decrease along this direction, in the cross sectional area of a portion of the cavity of a die through which the fluid is forced to flow. The 'direction of flow' in a portion of a die cavity is here defined as the direction along the axis of the said portion of the die cavity, in which fluid is on average transported. By the 'axis' of a portion of a die cavity is meant the line joining the centroids of the entrance and exit surfaces of the said portion of the die cavity. By a 'cross section' of a die cavity is meant a planar section perpendicular to the axis. A diverging flow is here defined as a flow in which the streamlines diverge in the direction of flow, as a result of an increase along this direction, in the cross sectional area of a portion of a cavity of a die through which the fluid is forced to flow. The definitions of this paragraph are illustrated in the Example described further on.

In the method of the present invention, extensional viscosity, elasticity and optionally shear viscosity of a fluid are determined from pressure measurements made on flows of the fluid at measured volume flow rates, through an aparatus containing an open ended die whose cavity includes a converging portion, a diverging portion and optional portions of constant cross sectional shape and size. (Die cavity portions of constant cross sectional shape and size are hereafter referred to as die cavity portions of constant cross section, or as constant cross section portions, or the like.)

The method of determination of extensional viscosity and fluid elasticity is based on the effects on pressure measurements, of reversible storage of elastic energy in converging flow, and of release of reversibly stored elastic energy in diverging flow. The geometric parameters of the die cavity and the sites of pressure measurements are so chosen (in conjunction with chosen fluid mechanical assumptions) that the said elastic storage and release effects are mutually compensing in relation to at least one function of the pressure measurements (e.g. a measured pressure difference between a point upstream from a point downstream from both of the converging/diverging portions). This makes possible a quantitative separation of pressure drop effects due to fluid elasticity on the one hand and pressure drop effects due, on the other hand, to the combination of shear and extensional viscosity. After the performance of the said separation, elasticity and extensional viscosity can be calculated.

In preferred embodiments of the apparatus of the present invention, the converging portion and the diverging portion of the die cavity are symmetrically shaped. It then follows, on the basis of certain fluid mechanical assumptions, that in any one steady flow of a fluid through the rheometer die, the elastic energy stored in flow in the converging portion is equal to the reversibly stored elastic energy released in flow in the diverging portion. Assuming that these changes in stored elastic energy can be linearly related to components of pressure drops measured between points upstream from and downstream from the respective converging or diverging flows, it follows that the storage and release effects are mutually compensating in relation to any measurement of a total pressure drop associated with flow through both the converging and diverging portions. On the basis of this, it is possible to separate the reversible elastic contributions to pressure drops measured over the individual converging and diverging portions, and hence to determine elasticity and extensional viscosity. This procedure is illustrated in the Example below. It will be appreciated that the preferred embodiments and the Example mentioned here do not limit the general principle of the invention; differently configured converging and diverging portions could be used in conjunction with different pressure measurements and different fluid mechanical assumptions, within the scope of the present invention, in such a way as to render elastic energy storage and release effects mutually compensating in relation to a function of the pressure measurements.

The pressure measurements associated with the converging and diverging flows are preferably made in portions of the die cavity of constant cross section which are adjacent to the converging and diverging portions, and which are situated upstream from, downstream from and inbetween the converging and diverging portions. These constant cross section portions are contained in preferred embodiments of the apparatus of the present invention, as described below.

The aforesaid contribution to pressure changes arising from elastic energy storage is used to determine fluid elasticity, and the corresponding contribution from the combined effects of shear and extensional viscosity is used to determine extensional viscosity. To perform this second determination, the contributions of shear and extensional viscosity must be quantitatively separated, and this requires modelling of the contribution from shear viscosity. The modelling requires a shear viscosity characterisation of the fluid at the relevant temperature. This characterisation can be obtained either from an independent experiment or, as is preferred, from the optional in-line shear viscosity determination of the present invention.

Shear viscosity is used to model the shear flow contribution to the viscous contribution to the total pressure drops associated with the converging and diverging flows. It is also used to model the shear flow viscous pressure drop in those parts of constant cross section die cavity portions which lie between the points of pressure measurement and the entrance or exit surfaces of the adjacent converging and/or diverging portion(s).

Determination of shear viscosity requires measurement of pressure differences along the direction of flow in a portion of the die cavity having constant cross section along the direction of flow. In the optional determination of shear viscosity according to the present invention, the pressure gradient is measured along one or more die cavity portions of constant cross section. These portions may be, but are not necessarily, any of the portions of constant cross section adjacent to the converging and diverging portions, as described above.

It is preferred in the method of the present invention that measurements of pressure are made on steady state flows. These are flows in which conditions at any fixed point in the apparatus have become substantially time invaraint. A steady state of flow can be achieved by the imposition of a constant fluid displacement rate by a fluid delivery system used to force fluid through the die, for a sufficient length of time that transient effects due to the compressibility of the fluid decay to an insignificant level. The transient effects can be modelled by a suitable adaptation of Equation 36 of a scientific paper by J. M. Lupton and J. W. Regester (Polymer Engineering and Science, Vol. 5, p. 265, 1965). This makes possible a calculation of the 'sufficient length of time' in any given case. The method of the present invention also includes measurements on flows that arise from any temporal programme of applied fluid displacement rates.

It is further preferred in the method of the present invention that pressure measurements are made on steady state flows at several volume flow rates at the same temperature. This gives the advantage that elasticity, extensional viscosity and shear viscosity (if determined) can be determined at a range of values of their independent variables (e.g. shear stress, extension rate, shear rate). It also gives the advantage, in cases in which shear viscosity is determined, that a Rabinowitsch correction can be performed on the measured data, so giving a more accurate determination of shear viscosity.

The determination of the rheological properties from the measured data is made using equations based on the above principles. Suitable equations for this purpose can be derived by persons knowledgeable in the science of rheology. Examples of such equations are provided in the Example described further on, but these should not be construed in any such way, as to limit the scope of the present invention to the use of these equations or any other specific set of equations.

In the method defined in the present invention for the determination of fluid elasticity from the elastic contribution to measured pressure differences, a pressure difference associated with storage of elastic energy in a converging flow is found, that has an intrinsic correction for viscous and irreversible elastic contributions.

In the determination of extensional viscosity by the method of the present invention, a pressure difference associated with a converging flow is found, that has an intrinsic correction for contributions from reversible storage of elastic energy. The shear flow contribution to the total pressure drop associated with the converging or diverging flow can be modelled and thence subtracted out using shear viscosity data determined from in-line pressure measurements; this overcomes errors that might otherwise arise from batch-to-batch and shot-to-shot variations in fluid properties. Pressure differences due to shear flow in those parts of constant cross section die cavity portions that lie between the points of pressure measurement and the adjacent entrance or exit surface(s) to the converging and/or diverging portion(s) can be modelled and subtracted out using the same viscosity data as above, with the same attendant benefit.

The method and apparatus of the present invention have the further advantage of combining in one rheometer the capabilities for determination of up to three rheological properties, namely elasticity, extensional viscosity and shear viscosity.

In the apparatus of the present invention, it is preferred that the diverging portion is downstream from the converging portion.

It is further preferred that the shape of the diverging portion is a reflection of the shape of the converging portion, about a plane that is parallel to a cross sectional plane of the converging portion and which passes through a point midway between the converging and diverging portions. That is to say, the converging and diverging portions are symmetrically shaped.

It is further preferred that the converging and diverging portions are separated by an intervening constant cross section portion, whose cross section is such that, at the connecting surface between the converging portion and the constant cross section portion, and at the connecting surface between the constant cross section portion and the diverging portion, the perimeters of the adjoining portions are continuous. This property is hereinafter referred to as continuous connection.

It is further preferred that the entrance surface of the upstream converging or diverging portion and the exit surface of the downstream converging or diverging portion connect respectively to exit and entrance surfaces of die cavity portions of constant cross sectional shape.

The constant cross section die cavity portions of the preferred embodiments described above should be of sufficient length along the direction of flow, that a state of flow can be attained in which substantial relaxation has occurred, of stresses and strains associated with the transients that occur in flow into and out of the constant cross section portion. The lengths required to satisfy this requirement can be estimated, for example, by a method described in a scientific paper by R. A. Worth and J. Parnaby (Transactions of the Institution of Chemical Engineers, Vol. 52, p. 368, 1974).

It is further preferred that the cross sectional shapes of the converging portion, of the diverging portion and of all portions connecting to the converging and diverging portions are of the same general type, most preferably circular or rectangular slit. A rectangular slit shape is a rectangular shape in which the length far exceeds the breadth. In practical terms related to the present invention, the ratio of length to breadth should be greater than or equal to 5:1, in order to ensure a reasonable approximation to rectangular slit flow. However, it will be appreciated that the present specification includes all conceivable cross sectional shapes.

It is preferred that the walls of the die cavity are unlubricated, as is implicit in the foregoing description. However a rheometer in which the die walls are lubricated with a material such as an oil, wax or grease is an option in the present invention.

By the term 'pressure', as used in the present specification, is meant the normal force per unit area encountered at a surface in the fluid. This definition is not the same as the definition of hydrostatic pressure for stationary fluids, in that it includes normal stress measurements on flowing fluids. An optional technique of pressure measurement in the present invention is that of stress optical measurement. It will be appreciated that a form of pressure measurement as herein defined is a measurement of the total head pressure, as provided for example by a piston to force fluid through the rheometer die system.

The preferred technique of pressure measurement in the apparatus of the present invention is the use of wall mounted pressure transducers of the deformable diaphragm type. It is preferred that the pressure actuated diaphragms are flush, or as nearly as possible flush, with the die wall. Dynisco Plastic Melt Pressure Transducers are examples of suitable instruments for this application.

In the case of wall pressure measurements in die cavity portions of rectangular slit cross sectional shape, it is preferred that the points of pressure measurement should be central. That is to say, the said points should be equispaced between the shorter dimension sides of the rectangular slit shaped cross sectional perimeter.

The preferred points of measurement of pressures associated with the converging and diverging flows are in three constant cross section portions adjacent to the converging and diverging portions, i.e. the upstream, downstream and intervening portions that are referred to above.

The preferred points of pressure measurement in respect of the optional determination of shear viscosity are in any constant cross section die cavity portion. To facilitate shear viscosity determination, at least two pressures must be measured in any such portion, at points differently spaced from the entrance to the die cavity portion.

Where pressure transducers are sited in a constant cross section die cavity portion, it is preferred that the pressure transducer wells are separated from both the entrance and the exit surfaces of the die cavity portion, by distances great enough to allow substantial relaxation of stresses and strains associated with the transients that occur in the flows into and out of the constant cross section portion. This method of estimating the required distances is that mentioned above.

It will be apparent that pressure measuring instruments can be so placed, that shear viscosity can be determined in more than one of the constant cross section die cavity portions. It will also be apparent that pressure measuring instruments can be sited in some or all of the constant cross section portions, in such a way that their measurements can be used in relation both to shear viscosity determination and to the converging and/or diverging flows in adjacent portions.

It is necessary that some form of fluid delivery system is provided in conjunction with the die of the apparatus of the present invention. This must be capable of delivering the fluid under investigation to the die cavity, at the required temperature, at sufficient total head pressure, and at a continuous range of constant, measured volume flow rates. Optionally the delivery system may also be able to provide a variable, programmed volume flow rate. In the case of a constant volume flow rate, sufficient volume of fluid should be provided by the delivery system in any single shot, that a steady state of flow is attained. A steady state is not attained immediately, because of the compressibility of the fluid. The 'sufficient volume' can be calculated by using the quantitative approach to compressibility transient modelling, described above. An example of a suitable delivery system is a hydraulically driven ram extrusion device such as is found as a part of certain types of injection moulding machine. Monitoring of the volume flow rate can be accomplished in this case by measurement of the displacement rate of the ram by a low voltage displacement transducer.

It is necessary that the die of the apparatus of the present invention is provided with a system for controlling its temperature to the required temperature of the fluid under test. It is also advantageous that the die is provided with fluid contacting thermocouples to monitor the actual fluid temperature.

It is advantageous that all the measurements of pressure, temperature and volume flow rate that are made in any flow in the rheometer are translated into electrical signals and interfaced, by means of analogue to digital conversion, to a minicomputer, microcomputer or other computer, for the purpose of automatic data acquisition and processing. It is further advantageous that the operation of the rheometer is controlled by servo mechanisms actuated by analogue signals converted from the digital output of the same computer. Thus the rheometer can be both monitored and controlled by a computer.

EXAMPLE OF THE INVENTION

Figure 1:
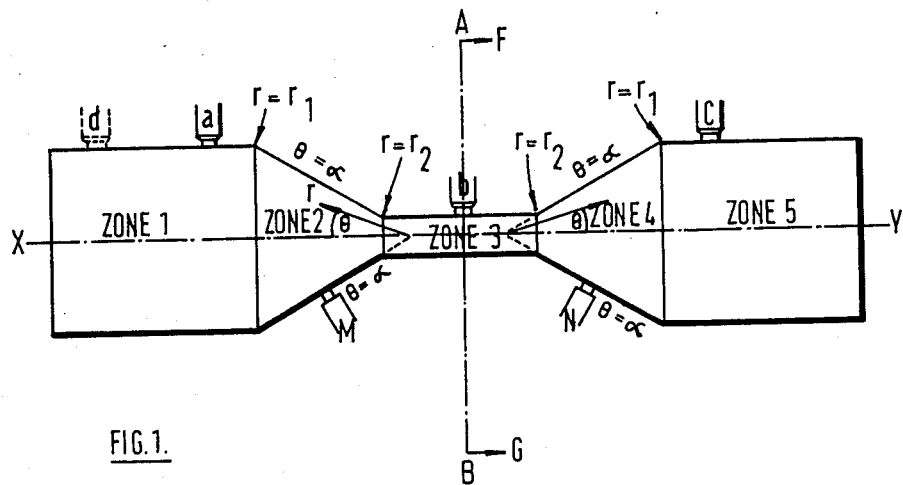
FIG. 1 shows the die cavity geometry of the rheometer.

FIG. 1 shows the die cavity geometry of an example of the apparatus of the present invention. Not shown are the fluid delivery system and details of the die cavity construction other than the cavity geometry and the transducer well sites. The line XY forms the 'axis', as herein defined, of all the portions of the die cavity, viz. Zones 1, 2, 3, 4 and 5. The 'direction of flow', as herein defined, is from X to Y, since the fluid delivery system connects with Zone 1. Thus Zone 2 is the converging die cavity portion and zone 4 is the diverging die cavity portion. 'Cross sectional planes', as herein defined, are planes normal to the line XY. All the cross sectional planes of all the die cavity portions are parallel to each other in the present Example.

Each of Zones 1, 3 and 5 is a zone of constant, circular cross sectional shape. The cross sectional plane passing through the line AB bisects Zone 3. The shape of Zone 4 is a reflection in this plane of the shape of Zone 2. Thus Zones 2 and 4 are symmetrically shaped. a, b and c are pressure transducer wells for wall mounted pressure transducer whose pressure actuated diaphragms are as nearly as possible flush with the die wall. M and N are wells for the seating of plugs containing fluid contacting thermocouples for fluid temperature measurement.

Figure 2:
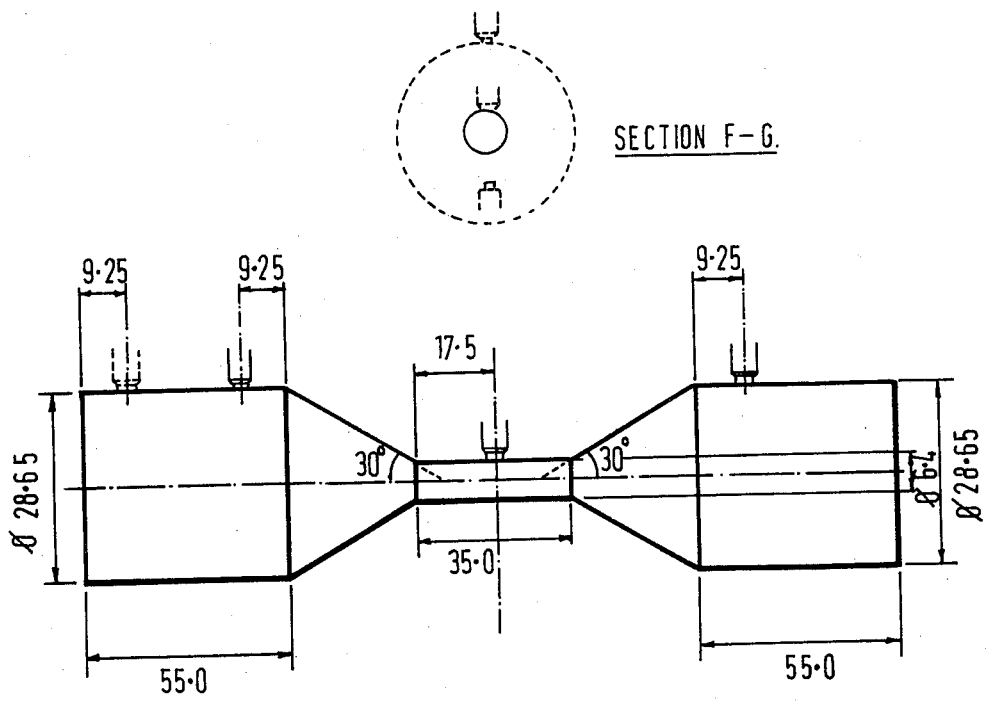
FIG. 2 shows the dimensions (in mm) of the rheometer of FIG. 1.

The dimensions (in mm) of Zones 1 to 5 and of the positions of the central axes of the pressure transducer wells a, b and c are shown in FIG. 2.

The following equations may be derived, from which it is possible to calculate shear modulus and extensional viscosity. The equations are not exact, but are reasonable approximations based on assumptions known by rheologists to be practically tenable. The elastic shear modulus is a function of shear stress $\tau$ and temperature T; it is written G or G($\tau$), with the temperature functionality omitted. The extensional viscosity is a function of extension rate $\dot{\epsilon}$ and temperature; it is written $\eta_e$ or $\eta_e(\dot{\epsilon})$, again with the temperature functionality omitted.

$$P_a - P_c = -2 \frac{\partial p}{\partial z}(a_1) l_a - 2 \frac{\partial p}{\partial z}(a_2) l_b + 2\Delta P_c + \delta \quad (1)$$

$$P_a - 2P_b + P_c = \frac{\tau a_1^2}{2G(\tau a_2/2)} - \frac{\tau a_1^2}{2G(\tau a_1/2)} \quad (2)$$

$$\frac{\partial p}{\partial z}(a_1) = -2k \left( \frac{q}{\pi} \frac{3n+1}{n} \right)^n \left( \frac{1}{a_2} \right)^{2n} \quad (3)$$

$$\frac{\partial p}{\partial z}(a_2) = -2k \left( \frac{q}{\pi} \frac{3n+1}{n} \right)^n \left( \frac{1}{a_2} \right)^{2n} \quad (4)$$

$$\Delta P_c = \frac{2k}{3na^{3n+1}} \left( \frac{q}{\pi} \frac{3n+1}{n} \right)^n \left( \frac{1}{r_2^{3n}} - \frac{1}{r_1^{3n}} \right) + \quad (5)$$

$$\frac{4q}{3\pi a^2} \left[ \frac{\eta_e(\bar{\epsilon}_2)}{r_2^3} - \frac{\eta_e(\bar{\epsilon}_1)}{r_1^3} \right]$$

$$\bar{\epsilon}_1 = \frac{2q}{\pi a^2 r_1^3} \quad (6)$$

$$\bar{\epsilon}_2 = \frac{2q}{\pi a^2 r_2^3} \quad (7)$$

$$\tau a_1 = -\frac{a_1}{2} \frac{\partial p}{\partial z}(a_1) \quad (8)$$

$$\tau a_2 = -\frac{a_2}{2} \frac{\partial p}{\partial z}(a_2) \quad (9)$$

$p_a$, $p_b$ and $p_c$ are the steady state pressures measured by pressure transducers mounted in the wells a, b and c respectively. q is the volume flow rate across the entrance surface to Zone 1. $1a$ is the distance in the XY direction between the axis of a and the boundary between Zones 1 and 2; i.e. $1a = 9.25$ mm. $1b$ is the distance in the XY direction between the axis of b and the boundary between Zones 2 and 3; i.e. $1b = 17.25$ mm. $1b$ is also the distance in the XY direction between the axis of b and the boundary between Zones 3 and 4. $1c$ is the distance in the XY direction between the axis of C and the boundary between Zones 4 and 5. $a_1$ is the cross sectional radius of Zones 1 and 5; i.e. $a_1 = 14.33$ mm. $a_2$ is the cross sectional radius of Zone 3; i.e. $a_2 = 3.2$ mm. r and $\theta$ are polar coordinates to which Zones 2 and 4 are referred, as indicated in FIG. 1. $\alpha$ is the half angle of the zone boundaries of Zones 2 and 4; i.e. at the boundaries $\theta = \pm \alpha$. In the present example $\alpha = \pi/6$.

$r_1$ is the value of r in Zone 2 at $\theta = \alpha$ and at the boundary with Zone 1; i.e. $r_1 = 28.65$ mm. $r_2$ is the value of r in Zone 2 at $\theta = \alpha$ and at the boundary with Zone 3; i.e. $r_2 = 6.4$ mm. Similar properties of $r_1$ and $r_2$ apply in Zone 4.

$\bar{\epsilon}_1$ is the $\theta$-average value of $\dot{\epsilon}$ at $r=r_1$ in Zones 2 and 4. $\bar{\epsilon}_2$ is the $\theta$-average value of $\epsilon$ at $r=r_2$ in Zones 2 and 4.

$\delta$ is a small term accounting for irreversible pressure drop contributions from the transient flows near the zone boundaries, and for the irreversible elastic pressure drops in the converging and diverging flows.

$$\frac{\partial p}{\partial z}(a_1) \text{ and } \frac{\partial p}{\partial z}(a_2)$$

are the pressure gradients due to shear viscosity in flow in constant circular cross section die cavity portions of radii $a_1$ and $a_2$ respectively.

$\Delta p_{cv}$ is the pressure drop due to shear and extensional viscosity in the converging flow in Zone 2; $\Delta p_{cv}$ is also equal to the pressure drop due to shear and extensional viscosity in the diverging flow in Zone 4.

k and n are the 'power law' coefficients of the shear flow characterisation of the fluid. In the present Example, k and n are determined in an independent experiment. The 'power law' coefficients are obtained by a regression fit of the equation 'shear stress = k x (shear rate)$^n$' to (shear stress, shear rate) points obtained from viscometric data. k and n could be determined in a modification of the apparatus of the present Example, in which for example an extra pressure transducer was placed in the well location indicated 'd' in FIG. 1. The steady state pressure differences measured between d and a at various steady values of q could be used to determine k and n.

The rhs of Equation 1 is devoid of recoverable elastic energy terms, illustrating the general principle of the invention. $p_a-p_c$ is related to pressure drop effects due (apart from $\delta$) only to shear and extensional viscosity.

The rhs of Equation 2 is the sum of the magnitudes of reversible elastic pressure drop contributions in Zones 2 and 4. Thus by taking the respective functions $p_a-p_c$ and $p_a-2p_b+p_c$ of the measured pressures $p_a$, $p_b$ and $p_c$, it is possible to separate terms due to shear and extensional viscosity (i.e. the rhs of Equation 1) from terms due to reversible elasticity (i.e. the rhs of Equation 2). $\eta_e$ and G can subsequently be calculated.

The first two terms on the rhs of Equation 1 represent the sum of viscous pressure drops in flows along the constant cross section portions 1, 3 and 5, between pressure transducer well locations and adjacent entrance and exit surfaces of converging or diverging portions. The first term of the rhs of Equation 5 for $\Delta p_{cv}$ represents the pressure drop component in the converging and diverging flows, due to shear viscosity. Before $\eta_e$ can be calculated, all these shear viscosity terms must be evaluated. This is done via the 'power law' shear viscosity characterisation expressed by the constants k and n.

k and n are obtained from data measured either in an independent experiment (as in the present Example) or from in-line measurements, which could be taken in the above described modified form of the apparatus of the present Example.

Table 1 shows results obtained for melt flows through the die of the apparatus of the present Example, of ICI Alkathene XDG33 low density polyethylene at 195° C. Table 1 also shows the results of steps taken toward the calculation of $\eta_e$ and G.

$\Delta p_{cv}$ is obtained using Equation 1 neglecting $\delta$ and calculating values for the first two terms on the rhs from Equations 3 and 4. The power law coefficients k and n determined from an independent experiment are 19783.0 and 0.34424 respectively. The 'viscous component' is the calculated value of the first term on the rhs of Equation 5; this is subtracted from $\Delta p_{cv}$ to give the 'extensional component', i.e. the second term on the rhs of Equation 5. From this term, $\eta_e$ ($\epsilon_2$) is calculated, making the assumption $\eta_e(\epsilon_2)|r_2^3 >> \eta_e(\epsilon_1)|r_1^3$. $\epsilon_2$ is calculated from Equation 7, and so $\eta_e$ ($\epsilon$) can be inferred.

Figure 3:
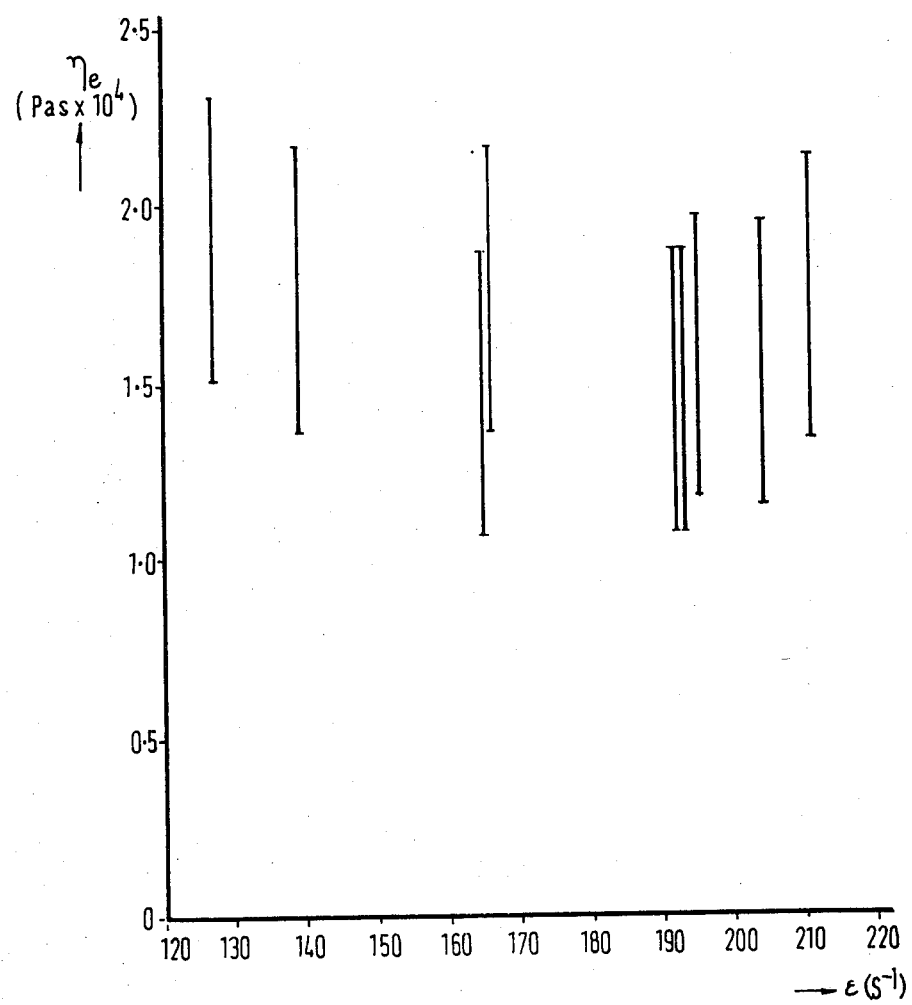
FIG. 3 is a plot of extensional viscosity vs. extensional rate.

$\eta_e$ is plotted as a function of $\epsilon$ in FIG. 3. The error bars are 95% confidence limits for $\eta_e$, estimated from a 1.6×full scale pressure transducer error. The graph shows a slight trend of decrease in $\eta_e$ with increasing $\dot\epsilon$. The extension rate range of 127 s$^{-1}$ to 211 s$^{-1}$ is higher than has ordinarily been available in the past, illustrating an advantage of the present invention.

The 1.6% pressure transducer error leads to an error in $p_a-2p_b+p_c$ of 0.88 MPa. Thus all the values of $p_a-2p_b+p_c$ in Table 1 lie within each other's error bar. No significant trend can be found in the results, and indeed the [($p_a-2p_b+p_c$), q] points have a correlation coefficient of 0.05. Accordingly, the data points are treated by calculating the centroid. The average $p_a-2p_b+p_c$ value is 2.79 MPa. The average q is $2.00\times 10^{-5}$ m$^3$s$^{-1}$. Thus from Equations 4 and 9, $\tau_{a3}=2.24\times 10^5$ Pa, and so from Equation 2, assuming $\tau_{a2}^2|G(\tau_{a2}|2) >> \tau_{a1}^2|G(\tau_{a1}|2)$, G $(1.12\times 10^5$ Pa$)=9.0\times 10^3$ Pa.

It is easy to see how G could be determined as a function of $\tau$, given more accurate values of $P_a-2p_b+p_c$. One way of achieving this would be to operate on the pressure transducer signal voltages at source, before amplification, to produce analogue signals to $P_a-2p_b+p_c$ and to $p_a-p_c$. Amplification of these, rather than voltages proportion to $p_a$, $p_b$ and $p_c$, would render more accurate values of $p_a-2p_b+p_c$ and $p_a-p_c$. Greater accuracy could also be achieved by better design; the data of the present Example were obtained in a first prototype experiment, and do not represent the limits of design of the apparatus of the invention.

TABLE 1

| q (m³ s⁻¹) | $p_a$ (MPa) | $p_b$ (MPa) | $p_c$ (MPa) | $p_a - p_c$ (MP) | $p_a - 2p_b + p_c$ (MPa) | $\Delta p_{cv}$ (MPa) | viscous component (MPa) | extensional component (MPa) | $\overline{\eta_e(\epsilon_2)}$ (Pa s) | $\overline{\epsilon_2}$ (s⁻¹) |
|---|---|---|---|---|---|---|---|---|---|---|
| 1.43 × 10⁻⁵ | 17.67 | 12.11 | 8.96 | 8.71 | 2.41 | 2.16 | 0.55 | 1.61 | 1.91 × 10⁴ | 127 |
| 1.57 × 10⁻⁵ | 18.34 | 12.42 | 9.46 | 8.88 | 2.96 | 2.17 | 0.57 | 1.60 | 1.73 × 10⁴ | 139 |
| 1.86 × 10⁻⁵ | 19.25 | 13.20 | 9.99 | 9.26 | 2.84 | 2.22 | 0.61 | 1.61 | 1.47 × 10⁴ | 165 |
| 1.87 × 10⁻⁵ | 20.27 | 13.79 | 10.31 | 9.96 | 3.00 | 2.57 | 0.61 | 1.96 | 1.77 × 10⁴ | 166 |
| 2.17 × 10⁻⁵ | 21.03 | 14.48 | 10.89 | 10.14 | 2.96 | 2.53 | 0.64 | 1.89 | 1.48 × 10⁴ | 192 |
| 2.18 × 10⁻⁵ | 21.03 | 14.51 | 10.84 | 10.19 | 2.85 | 2.55 | 0.64 | 1.91 | 1.48 × 10⁴ | 193 |
| 2.20 × 10⁻⁵ | 21.45 | 14.79 | 10.96 | 10.49 | 2.83 | 2.69 | 0.64 | 2.05 | 1.58 × 10⁴ | 195 |
| 2.30 × 10⁻⁵ | 21.10 | 14.61 | 10.89 | 10.71 | 2.77 | 2.77 | 0.65 | 2.12 | 1.56 × 10⁴ | 204 |
| 2.38 × 10⁻⁵ | 21.34 | 14.87 | 10.86 | 10.48 | 2.46 | 2.62 | 0.66 | 1.96 | 1.75 × 10⁴ | 211 |

Optional features of the method aspect of the invention are as follows:
- the determined values of the shear viscosity are used in the calculation of extensional viscosity; and/or
- the pressure measurements are made on steady state flows at several volume flow rates at the same temperature.

Optional features of the apparatus aspect of the invention include one or more of the following:
- the diverging portion is downstream from the converging portion;
- the cross sectional shapes of the converging portion(s), of the diverging portion(s) and of the constant cross section portion(s) are of the same general type;
- the cross sectional shapes of the converging portion(s), of the diverging portion(s) and of the constant cross section portion(s) are circular;
- the cross sectional shapes of the converging portion(s), of the diverging portion(s) and of the constant cross section portion(s) are rectangular slit;
- some or all of the pressures to be measured are measured by instruments mounted in such a way as to measure pressure centrally with respect to the longer side of a rectangular slit cross sectional shape;

the lengths along the direction of flow, of one or more of the die cavity portions of constant cross sectional shape, are sufficient that states of flow can be attained in which substantial relaxation has occurred of stresses and strains associated with the transients that occur in flow into and out of the respective constant cross section portions, the required lengths for this purpose being calculated by a method similar to that described in the proceding description;

some or all of the pressures to be measured are measured by pressure transducers of the deformable diaphragm type;

some or all of the diaphragm type pressure transducers are mounted in the die wall, in such a way that their pressure actuated diaphragms are flush, or as nearly as possible flush, with the die wall;

the fluid delivery system has sufficient capacity that a steady state of flow can be attained at all required volume flow rates. The method by which this condition can be designed is that described in the preceding description, in connection with fluid compressibility and steady state flow;

the fluid delivery system can provide a variable, programmed volume flow rate;

the fluid delivery system provides a continuous measurement of output volume flow rate;

the fluid delivery system provides a delivery of fluid at a preset, monitored temperature;

the die is maintained at a preset, monitored temperature;

the die temperature is the same as the temperature of the fluid injected into the die by the fluid delivery system;

the fluid temperature is monitored at one or more points in the die, by fluid contacting thermocouples;

some or all of the pressure, temperature and volume flow rate measurements are translated into electrical signals and interfaced, by means of analogue to digital conversion, to a microcomputer, minicomputer or other computer;

operation of the apparatus is controlled by a computer;

data provided by the apparatus is used in the calculation of rheological properties by means of a computer.

In the description and claims of this specification, the word "die" includes any suitable conduit: it does not need to be a die of an injection moulding machine or suitable for use in such a machine. The term "symmetrically shaped" relates in particular to pairs of converging and diverging portions of the die which portions are mirror images of each other. The term "continuously" used with reference to the shape of the die refers to a smooth translation from one portion of the die to an adjacent portion of the die or associated equipment without any sharp edge or other discontinuity between said adjacent portions.

What is claimed is:

1. A method of determination of extensional viscosity and elasticity of a visco-elastic fluid, said method comprising:

passing the fluid through an apparatus comprising a conduit having a converging portion and a diverging portion;

measuring the drop in fluid pressure resulting from flow through the converging portion, which pressure drop comprises contributions from fluid elasticity, extensional viscosity and shear viscosity;

measuring the change in fluid pressure resulting from flow through the diverging portion at predetermined sites wherein the increase in elastic energy of the fluid which occurs in the converging portion equals the decrease in elastic energy which occurs in the diverging portion, which pressure change comprises contributions from fluid elasticity, extensional viscosity and shear viscosity;

measuring the shear viscosity relationship of the fluid;

making a quantitative separation of those pressure change effects which are due to fluid elasticity and those which are due to a combination of extensional viscosity and shear viscosity;

and calculating the fluid elasticity and extensional viscosity relationships.

2. A method according to claim 1, in which the shear viscosity relationship is determined by making pressure measurements on flows of the fluid through one or more constant cross-section portions of said conduit.

3. A method according to claim 1 in which at least some of the pressure measurements associated with the converging and diverging flows are made in constant cross-section conduit portions, the said portions being sited adjacent the converging and diverging portions.

4. A method according to claim 1 in which pressure measurements are made on steady state flows corresponding to constant overall flow rates of fluid.

5. An apparatus for determining extensional viscosity and elasticity of a visco-elastic fluid, said apparatus comprising:

a conduit having a converging portion and a diverging portion, the converging and diverging portions being separated from each other by an intervening constant cross-section portion connecting to both continuously, and the entrance surface of the upstream converging (or diverging) portion and the exit surface of the downstream diverging (or converging) portion continuously connecting respectively to entrance and exit surfaces of conduit portions of constant cross-sectional shape;

a fluid delivery system connecting to one end of said conduit; and instruments for fluid pressure measurement and control of the temperature of the conduit, the instruments for the measurement of fluid pressure being sited to measure pressure at one or more points in some or all of the constant cross-section portions, said points being sufficiently spaced from both the entrance and exit surfaces of the respective constant cross-section portion(s), that substantial relaxation can occur of stresses and strains associated with the transients that occur in the flows into and out of the respective constant cross-section portion(s).

6. An apparatus according to claim 5 containing additional converging, diverging and constant cross-section conduit portions.

7. An apparatus according to claim 5 in which the conduit walls are lubricated with a material such as an oil, wax or grease.

* * * * *